US006090584A

United States Patent [19]
Iatrou et al.

[11] Patent Number: 6,090,584
[45] Date of Patent: Jul. 18, 2000

[54] BACULOVIRUS ARTIFICIAL CHROMOSOMES AND METHODS OF USE

[75] Inventors: Kostas Iatrou; Patrick J. Farrell, both of Calgary, Canada; Yoshifumi Hashimoto, Fushimi-ku, Japan

[73] Assignee: University Technologies International Inc., Calgary, Canada

[21] Appl. No.: 09/136,419

[22] Filed: Aug. 20, 1998

Related U.S. Application Data

[60] Provisional application No. 60/056,807, Aug. 21, 1997.

[51] Int. Cl.$^7$ .......................... C12P 21/00; C12N 15/86; C12N 5/10; C07H 21/04
[52] U.S. Cl. .................. 435/69.1; 435/320.1; 435/235.1; 435/348; 435/325; 435/236; 435/455; 435/456; 435/91.4; 435/91.42; 435/91.41; 536/23.1; 536/23.72
[58] Field of Search .............................. 435/69.1, 320.1, 435/235.1, 348, 325, 236, 456, 91.4, 91.42, 91.41, 455; 536/23.1, 23.72

[56] References Cited

U.S. PATENT DOCUMENTS

| | | | |
|---|---|---|---|
| 4,889,806 | 12/1989 | Olson et al. | 435/91.53 |
| 5,348,886 | 9/1994 | Lee et al. | 435/320.1 |
| 5,637,477 | 6/1997 | Spaulding et al. | 435/69.1 |

FOREIGN PATENT DOCUMENTS

WO96/40965  12/1996  WIPO.

OTHER PUBLICATIONS

Bonning and Hammock, (1995) "Use of juvenile hormone esterase as a novel reporter enzyme in the baculovirus expression system" *J. Vir. Method.* 51:103–113.
Fire et al., (1990) "A modular set of lacZ fusion vectors for studying gene expression in *Caenorhabditis elegans*" *Gene,* 93:189–198.
Grace (1967) "Establishment of a line of cells from the silkworm *Bombyx mori*" *Nature* 216:613.
Hashimoto et al., (1996), "Attenuation of *Bombyx mori* nuclear polyhedrosis for a gene transfer vector", p70 in Japan–Canada Cooperative Workshop.
Hashimoto et al., (1995) "Bioassay of the silkworm, *Bombyx mori,* using a temperature–sensitive mutant *Bombyx mori* nuclear polyhedrosis virus", *Bulletin of the Faculty of Textile Science* 19:37–41 [abstract].
Hashimoto et al., (1995) "Isolation of temperature–sensitive mutants of *Bombyx mori* nuclear polyhedrosis virus", *Japanese Journal of Applied Entomology and Zoology* 39(1):33–37 [abstract].
Iatrou et al. (1985) "Polyhedrin gene of *Bombyx mori* nuclear polyhedrosis virus", *J. Virol* 54(2):436–445.
Johnson et al., (1992) "A cellular promoter–based expression cassette for generating recombinant baculoviruses directing rapid expression of passenger genes in infected insects" *Virology* 190:815–823.
Koelle et al., (1991) "The Drosophila EcR gene encodes an ecdysone receptor, a new member of the steroid receptor superfamily" *Cell* 67:59–77.
Kunkel (1985), "Rapid and efficient site–specific mutagenesis without phenotypic selection," *P.N.A.S.,* 82:488–492.
Lu et al., (1997) "A baculovirus (*Bombyx mori* nuclear polyhedrosis virus) repeat element functions as a powerful constitutive enhancer in transfected insect cells" *J. Biol. Chem.* 272(49):30724–30728.
Maeda and Majima (1990), "Molecular cloning and physical mapping of the genome *Bombyx mori* nuclear polyhedrosis virus," *J. of General Virology,* 71:1851–1855.
Mounier and Prudhomme, (1986), "Isolation of actin genes in *Bombyx mori:* the coding sequence of a cytoplasmic actin gene expressed in the silk gland is interrupted by a single intron in an unusual position," *Biochimie,* 68:1053–1061.
Giordano and McAllister, (1990),"Optimization of the hygromycin B resistance–conferring gene as a dominant selectable marker in mammalian cells" *Gene,* 88:285–288.
O'Reilly et al., (1992), "Summary of baculovirus features relevant to expression vectors", *Baculovirus Expression Vectors: A Laboratory Manual,* New York W.H. Freeman and Co., pp. 27–29.
Philpott and Hammock (1990) "Juvenile hormone esterase is a biochemical anti–juvenile hormone agent" *Insect Biochem* 20(5):451–459.
Sambrook et al., *Molecular Cloning: A Laboratory Manual,* Cold Spring Harbor Laboratory (1982).
Passarelli et al., (1994) "A baculovirus gene involved in late gene expression predicts a large polypeptide with a conserved motif of RNA polymerases" *J. of Virology,* 68(7):4673–4678.
Shikata et al, (1998) "Isolation and characterization of a temperature–sensitive mutant of *Bombyx mori* nucleopolyhedrovirus for a putative RNA polymerase gene" *J. of General Virology* 79:2071–2078.
Gomi et al., (1997) "Deletion analysis of four of eighteen late gene expression factor gene homologues of the baculovirus, BmNPV" *Virology* 230:35–47.
Ahrens et al., (1997) "The sequence of the *Orgyia pseudotsugata* multinucleocapsid nuclear polyhedrosis virus genome" *Virology* 229:381–399.
Faktor and Kamensky, (1997) "Genomic localization and nucleotide sequence of the lef–8 gene of the *Spodoptera littoralis* nucleopolyhedrovirus", *Virus Genes* 15(1):9–15.

*Primary Examiner*—David Guzo
*Attorney, Agent, or Firm*—Burns, Doane, Swecker & Mathis, L.L.P.

[57] ABSTRACT

An baculovirus artificial chromosome is disclosed which has the lef-8 gene inactivated. The baculovirus artificial chromosome allows the cloning and expression of heterologous genes in insect and mammalian cells without killing the host cells. Also disclosed is an infectious baculovirus comprising the artificial chromosome and a cell containing the chromosome. Also disclosed is an insect cell which expresses the LEF-8 gene in the absence of a baculovirus chromosome. Also disclosed is a method to express heterologous proteins in eukaryotic cells using the baculovirus artificial chromosome.

22 Claims, 6 Drawing Sheets

KEY: ▶ = region of promoter activity
! = transcription termination region
→ = transcribed open reading frame

FIG. 4A wtBmNPV

FIG. 4B

BVAC#1.LacZ

FIG. 4C

BVAC#2.LacZ

FIG. 5

SEQUENCE LISTING

<160> NUMBER OF SEQ ID NOS: 8

<210> SEQ ID NO 1
<211> LENGTH: 24
<212> TYPE: DNA
<213> ORGANISM: Bombyx mori

<400> SEQUENCE: 1
caaaggatcc gatgacggac gtag          24

<210> SEQ ID NO 2
<211> LENGTH: 31
<212> TYPE: DNA
<213> ORGANISM: Bombyx mori

<400> SEQUENCE: 2
cttttctaga gttatcaatt tttcattatc g          31

<210> SEQ ID NO 3
<211> LENGTH: 25
<212> TYPE: DNA
<213> ORGANISM: Bombyx mori

<400> SEQUENCE: 3
gaaggcagct gcggccctca cgcgt          25

<210> SEQ ID NO 4
<211> LENGTH: 38
<212> TYPE: DNA
<213> ORGANISM: Bombyx mori

<400> SEQUENCE: 4
ggaggagctc ttgcacgatt gcaaacatga taaaaccg          38

<210> SEQ ID NO 5
<211> LENGTH: 41
<212> TYPE: DNA
<213> ORGANISM: Bombyx mori

<400> SEQUENCE: 5 gggggagct cgtaaagcga ttattgcaca ctaattatgt c          41

<210> SEQ ID NO 6
<211> LENGTH: 29
<212> TYPE: DNA
<213> ORGANISM: Bombyx mori

<400> SEQUENCE: 6
gaaagggtac cgtcgcggac catacgttc          29

<210> SEQ ID NO 7
<211> LENGTH: 24

-continued

```
<212> TYPE: DNA
<213> ORGANISM: Bombyx mori

<400> SEQUENCE: 7
accctcacta aagggaacaa aagc                                              24

<210> SEQ ID NO 8
<211> LENGTH: 21
<212> TYPE: DNA
<213> ORGANISM: Bombyx mori

<400> SEQUENCE: 8
ctttgagctc gaggtcgacg g                                                 21
```

BACULOVIRUS ARTIFICIAL CHROMOSOMES AND METHODS OF USE

CROSS-REFERENCE TO RELATED APPLICATIONS

This application claims priority to U.S. Provisional Patent Application Ser. No. 60/056,807, filed Aug. 21, 1997 which is incorporated herein in its entirety.

BACKGROUND OF THE INVENTION

1. Field of the Invention

The present invention relates to genetically engineered baculoviruses substantially incapable of producing the baculovirus LEF-8 RNA polymerase subunit and eukaryotic cells infected with such baculoviruses. Such baculoviruses comprise an engineered chromosome in which the lef-8 gene has been inactivated or deleted. The invention is also related to methods for expressing heterologous proteins in cells using such baculovirus artificial chromosomes.

2. Description of the Related Art

The insect order of Lepidoptera includes all butterflies and moths, such as the silkmoth *Bombyx mori* and the alfalfa looper *Autographa californica*. Lepidopteran insects are host organisms for some members of a family of viruses, known as baculoviruses (more than 400 known species), that infect a variety of arthropods. In nature a baculovirus enters a lepidopteran insect host when a proteinaceous structure containing the virus, known as an "occlusion body" or "polyhedrin", is ingested with food. Once the occlusion body is dissolved in the insect gut, freed virus particles enter the host cells. This is followed by replication of viral genomic DNA, and by the generation and release of viral progeny for infection of other host insect tissues. The infection process terminates with the formation of occluded viruses prior to host cell death.

After the insect dies from infection, occlusion bodies containing virus are released from the dead larvae into the environment and spread the infection to other insects through contamination of the food supply. These occlusion bodies serve to protect the virus particles in the environment and also provide a means of delivering the virus particles to the primary site of infection in insects, the midgut epithelial cells.

Secondary infection within the insect involves the budded form of the virus. Viral nucleocapsids are synthesized in the nucleus of the insect cell, move through the cytoplasm and bud from the plasma membrane of the cell resulting in the release of budded virus particles into the insect hemolymph. The open circulatory system of the insect provides the virus with access to other tissues of the insect.

The synthesis of the budded and occluded forms of the virus is temporally regulated. During a typical infection of host tissue culture cells, progeny budded viruses are released into the culture media beginning approximately 12 hours post infection (p.i.) and the release continues logarithmically through 22 hours p.i. Occluded virus forms approximately at 20 hours p.i. and continues through 70 hours p.i. by which time approximately 70–100 polyhedral occlusions have formed in the nucleus. This temporal regulation of viral development is reflected in the controlled transcription of specific viral genes.

Figure 1:
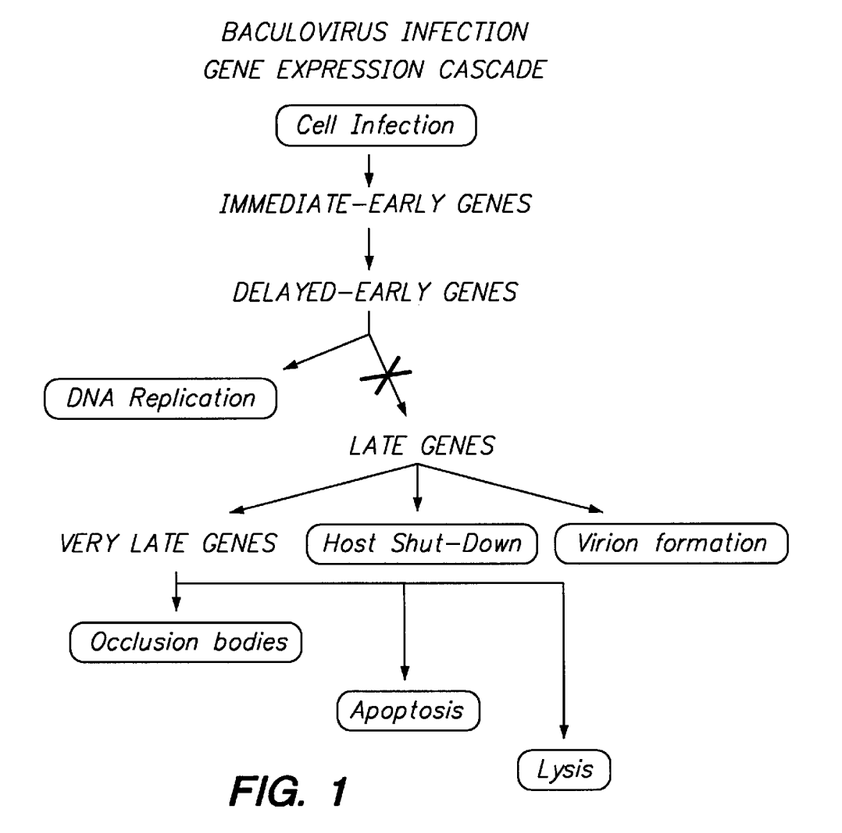
FIG. 1 illustrates the life cycle of a baculovirus; an early phase occurring after infection of the host cell and terminating with DNA replication; and a late phase that occurs after DNA replication and produces new viral particles, occluded virus and cell death. The blocking of a control function is indicated by the large X.

Baculoviruses, specifically nuclear polyhedrosis viruses (NPVs) have a unique life cycle which involves the temporally regulated expression of different genes. Nuclear polyhedrosis virus genes are transcribed in a regulated cascade involving at least three phases of transcription: an early phase (0–6 hours p.i.) prior to viral DNA replication, a late phase (6–18 hours p.i.) involving DNA replication and budded virus formation and the very late occlusion phase (18 through 70 hours p.i.). See FIG. 1.

Hashimoto et al., (1996), "Attenuation of *Bombyx mori* nuclear polyhedrosis for a gene transfer vector", p70 in Japan-Canada Cooperative Workshop disclosed a temperature sensitive mutant *Bombyx mori* NPV which underwent DNA replication but did not produce extracellular virus and polyhedra. Hashimoto indicated that the mutations were within a genomic region of 7.3 mu to 32.5 mu which contained the p47, p39 and lef11 AcNPV gene homologues.

To date, the study of lepidopteran insects and commercial biotechnology applications using lepidopteran insects or in vitro cell cultures derived from such insects, has been hampered by the lack of a suitable method to permanently introduce genes into the host (a stable gene transformation or transduction system).

In contrast, successful gene transformation systems have been developed for non-lepidopteran insect species, such as the fruit fly *Drosophila melanogaster*, where P element-based embryo transformation vectors have led to an explosion in the understanding of the complex genetic processes involved in the fruit fly life cycle.

A novel stable gene transduction (or transformation) methodology that allows the generation of (1) transgenic lepidopteran insects that can be used for basic research, recombinant protein production and biopesticide industry-related applications, (2) in vitro transduced lepidopteran insect cell cultures for large scale production of recombinant proteins would be advantageous, and (3) in vivo DNA vaccination and gene therapy would be desirable.

It has now been found that the inactivation or deletion of the lef-8 gene from the baculovirus genome allows the baculovirus genome to replicate but not to kill the insect cell or form occlusion bodies. Thus the baculovirus artificial chromosome cannot productively infect insect cells. Such recombinant baculovirus genomes can function as artificial chromosomes for the production of recombinant proteins in insect cells.

The baculovirus genome encodes its own RNA polymerase enzyme which is composed of a number of different subunits. One of the baculovirus genes encoding a RNA polymerase-like subunit, LEF-8, of the *Bombyx mori* nuclear polyhedrosis virus (BMNPV) genome has been identified and sequenced (Genbank Accession Number L33180:ORF #39). This gene is conserved among all the characterized baculoviruses. For example, the equivalent gene in *Autographa californica* (AcMNPV), encoded by open reading frame (ORF) #50, has also been sequenced (GenBank Accession number L22858), as has the gene of *Orgyia pseudotsugata* (OpMNPV), encoded by ORF #54 (GenBank Accession Number U75930).

Further advantages of the present invention will become apparent from the following description of the invention with reference to the attached drawings.

SUMMARY OF THE INVENTION

The present invention is directed to genetically engineered baculoviruses lacking a functional gene (lef-8) which encodes an active subunit of the baculovirus RNA polymerase. Such baculoviruses can act as artificial chromosomes for the expression of foreign proteins in cells.

This invention is directed to a baculovirus artificial chromosome lacking a gene which encodes an active LEF-8 protein. The chromosome may lack the lef-8 gene entirely or comprise an inactivated lef-8 gene. Preferably, the chromosome may further comprise a heterologous gene and/or a detectable marker gene. The baculovirus artificial chromosome may be derived from the genome of BmNPV, AcNPV, OpNPV or any other baculovirus containing a lef-8-like gene.

This invention is also directed to a cell comprising the baculovirus artificial chromosome. The cell may be a eukaryotic cell or a prokaryotic cell. If the cell is a eukaryotic cell, it is preferably an insect cell or a mammalian cell.

This invention is also directed to an insect cell which comprises and expresses the lef-8 gene in the absence of a baculovirus chromosome and wherein the insect cell produces active LEF-8 protein.

This invention is also directed to a method of making an baculovirus artificial chromosome, said method comprising inactivating the lef-8 gene of the baculovirus genome.

This invention is also directed to a method of expressing a heterologous gene in a eukaryotic cell, said method comprising propagating a eukaryotic cell comprising one or more copies of a baculovirus artificial chromosome lacking a gene which encodes an active LEF-8 protein wherein said chromosome further comprises a DNA sequence encoding a heterologous gene, under conditions that allow expression of the heterologous gene. Preferably the cell is an insect cell or a mammalian cell.

BRIEF DESCRIPTION OF THE DRAWINGS

FIG. 3 illustrates the construction of the wild-type BmNPV fragment containing the lef-8 open reading frame and the construction of five transfer vectors having an inactivated or deleted lef-8 gene but containing the 5' and 3' flanking regions of the lef-8 open reading frame: TV#1. LacZ containing a cassette comprising the lacZ open reading frame inserted into the actin expression cassette and then inserted into the lef-8 open reading frame to inactivate it; TV#2. LacZ containing a cassette comprising the lacZ gene inserted into the actin expression cassette and inserted between the 5' and 3' flanking regions of the lef-8 open reading frame; TV#3. LacZ containing the lacZ gene inserted between the 5' and 3' flanking regions of the lef-8 open reading frame; TV#2. jhe containing a cassette comprising the jhe gene inserted into the actin expression cassette and then inserted between the 5' and 3' flanking regions of the lef-8 open reading frame; TV#3.jhe containing the jhe gene inserted between the 5' and 3' flanking regions of the lef-8 open reading frame.

FIG. 4 is a photograph of Bm5 cells 3 days after infection with either (FIG. 4A) wild-type BmNPV (wtBmNPV) or the recombinant baculoviruses: (FIG. 4B) BVAC#1.LacZ or (FIG. 4C) BVAC#2.LacZ. The cells were held at 28° C.

DETAILED DESCRIPTION OF THE INVENTION

The present invention is directed to genetically engineered baculoviruses in which the gene encoding a subunit of the baculovirus RNA polymerase is either inactivated or deleted. Such baculoviruses can act as artificial chromosomes for the expression of foreign proteins in cells.

However, prior to discussing this invention in further detail, the following terms will first be defined.

Definitions

The term "baculovirus chromosome" refers to the genome of the baculovirus, which genome is circular. In a preferred embodiment, the baculovirus chromosome is derived from the B. mori nuclear polyhedrosis virus. In another embodiment, the chromosome is derived from the A. californica nuclear polyhedrosis virus or any other nuclear polyhedrosis virus that contains a lef-8 gene or lef-8-like gene.

The term "baculovirus artificial chromosome" or "(BVAC)" refers to an engineered baculovirus chromosome which is able to autonomously replicate in an insect cell, but which is unable to kill the insect cell because the baculovirus artificial chromosome lacks a gene which encodes an active protein which is substantially identical to the LEF-8 protein that is encoded by BmNPV ORF #39 (GenBank Accession Number L33180). In a preferred embodiment the baculovirus chromosome replicates autonomously in insect cells at any temperature without killing the insect cells.

The lef-8 gene includes any baculoviral gene which performs the same functions as the BmNPV lef-8 gene or which has a nucleic acid sequence which is substantially similar to the BmNPV lef-8 gene (GenBank Accession Number L33180: ORF #39). Preferably the lef-8 gene encodes an active protein that is at least 60% identical to the LEF-8 protein that is encoded by BmNPV ORF #39; more preferably the protein is at least 75 % identical to the LEF-8 protein and most preferably it is at least 90% identical. Included within the definition of the lef-8 gene is the lef-8 genes of AcNPV (GenBank Accession Number L22858: ORF #50) and OpNPV (GenBank Accession Number U75930: ORF #54).

A baculovirus chromosome or baculovirus "lacks a gene that encodes an active LEF-8 protein" when the chromosome or baculovirus does not produce, in infected cells, the LEF-8 protein or produces the protein in a form which is inactive. Such a chromosome can be made by deleting the lef-8 gene from the chromosome or by disrupting the lef-8 gene. Disruption of the lef-8 gene can occur, for example, by insertion of another piece of DNA sequence into the lef-8 gene or by deletion of part of the lef-8 gene open reading frame.

"Replication" means the process of production of a new DNA strand using a DNA template strand for the copying of the information content of the genome. A baculovirus chromosome which is capable of replication is capable of initiating the reproduction of its genome in the host cell.

A baculovirus chromosome which is incapable of killing an insect cell means that certain baculoviral proteins encoded by the native baculovirus chromosome are not produced, which proteins are necessary for virus packaging and cell death of a wild-type insect cell. These proteins include the majority of the late viral proteins, for example, polyhedrin.

The cell or host cell may be prokaryotic or eukaryotic. If the cell is eukaryotic, it is preferably an insect cell or a mammalian cell.

The term "insect cells" means insect cells from the insect species which are subject to baculovirus infection. For example, without limitation: *Autographa californica; Bombyx mori; Spodoptera frugiperda; Choristoneura fumiferana; Heliothis virescens; Heliothis zea; Helicoverpa zea; Helicoverpa virescens; Orgyia pseudotsugata; Lymantria dispar; Plutella xylostella; Malacostoma disstria; Trichoplusia ni; Pieris rapae; Mamestra configurata; Mamestra brassica; Hyalophora cecropia*.

An insect cell comprising a lef-8 gene "in the absence of a baculovirus chromosome" means that the cell contains the lef-8 gene, such that the insect cell produces the LEF-8 protein, but does not contain a complete baculovirus chromosome.

It is contemplated that the expression of the lef-8 gene in the cell may be either constitutive expression or induced by the application of environmental factors. Suitable means of inducing expression of the lef-8 gene include temperature for copies of the gene placed under the control of a heat shock promoter. Alternatively, the lef-8 gene may be functionally linked to a control element such that the cell must be exposed to a compound for expression of the lef-8 gene. For example, the lef-8 gene may be linked to a gal4 promoter such that expression of the lef-8 gene occurs upon exposure to galactose.

The term "transplacement fragment" means a DNA fragment which comprises: (1) a recombinant DNA sequence, and (2) a portion of a baculovirus genome. The term "a portion of a baculovirus genome" means a portion of the genome of sufficient size to allow recombination events to occur between the transplacement vector and a wild type baculovirus genome such that the recombinant DNA fragment is inserted into the genome. One skilled in the art would know the size of the baculovirus flanking sequences necessary to allow recombination events. Preferably, the size of the baculovirus flanking sequences are at least about 500 bp on each side of the recombinant DNA sequence, more preferably, the size of the flanking sequences is at least about 5,000 bp on each side.

The term "transplacement vector" or "transfer vector" means nucleic acid which comprises: (1) a transplacement fragment, and (2) DNA sequences allowing replication and selection in bacteria, for example *E. coli*. The vector may be a plasmid, another virus or simply a linear DNA fragment. A transplacement fragment or vector is used to produce recombinant baculoviruses through double recombination/cross-over events. When insect cells are transfected with the transplacement vector and DNA from wild-type baculovirus, a double cross-over event between the homologous portions of the baculovirus genome and the transplacement fragment will result in the replacement of a portion of the wild-type baculovirus sequence with a part of the transplacement fragment.

Detectable markers are genes which allow detection of cells that have been transfected or infected with the gene. Detectable markers include reporter genes and selection genes. Reporter gene are genes which confer a characteristic onto the cell which is detectable. Suitable reporter genes include the gene encoding for green fluorescent protein, the β-galactosidase gene and the chloramphenicol acetyl transferase gene. Selection genes are wild-type alleles of genes that encode for enzymes which allow the cell to grow on certain media, such as media containing antibiotics. These genes include, for example, the prokaryotic hygromycin resistance and neomycin resistance genes.

The DNA and chromosomes have been developed especially for use as expression vectors for protein production and other purposes. Therefore, in a preferred embodiment, the baculovirus artificial chromosome also contains one or more DNA sequences useful for the expression of a desired gene product. The invention is thus directed to a method for introducing expressible DNA into a cell by including this DNA on the artificial chromosome. When used for infection of cells, the artificial chromosomes harbor and express these DNA sequences.

The terms "producing heterologous protein" or "expressing heterologous protein" means that the structural gene encoding the heterologous protein is transcribed into mRNA and that the mRNA is further translated into protein. In a preferred embodiment the heterologous protein will be properly processed by the eukaryotic cell, although such processing may be in a tissue specific manner.

The term "structural gene" refers to those DNA sequences which, when functionally attached to a cellular or viral promoter, will be transcribed and produce a heterologous protein in insect cells.

The term "heterologous structural gene" or "heterologous gene" is a structural gene which is not normally present in wild-type baculovirus genomes. A heterologous structural gene is a structural gene which will be transcribed and will produce a protein when functionally attached to any promoter capable of functioning in the host cell or to an enhancer and promoter where the structural gene is present in a baculovirus artificial chromosome and thereafter introduced into eukaryotic cells either by infection of cells by the baculovirus artificial chromosome containing the heterologous gene or by transfection by a transfer vector. While the β-galactosidase ("LacZ") gene and the juvenile hormone esterase genes were used to characterize the expression of a heterologous protein under the control of the promoter in the examples provided herein, it will be recognized that any heterologous structural gene meeting the above criteria may be used in the invention.

The term "heterologous protein" refers to a protein encoded by a heterologous structural gene and which is not normally expressed by the baculovirus. Examples of heterologous proteins are chloramphenicol acetyltransferase, human alpha interferon (IFN-α), insulin-like growth factor-II (IGF-II), human interleukin 3, mouse interleukin 3, human and mouse interleukin 4, human T-lymphotropic virus (HTLV-1) $p40^x$, HTLV-1 env, human immunodeficiency virus (HIV-1) gag, pol, sor, gp4l, and gp120, adenovirus E1a, Japanese encephalitis virus env (N), bovine papilloma virus 1 (BPV1) E2, HPV6b E2, BPV1 E6, and human apolipoproteins A and E; β-galactosidase, hepatitis B surface antigen, HIV-1 env, HIV-1 gag, HTLV-1 $p40^x$, human IFN-β, human interleukin 2, c-myc, D. melanogaster Kruppel gene product, bluetongue virus VP2 and VP3, human parainfluenza virus hemagglutinin (HA), influenza polymerases PA, PB1, and PB2, influenza virus HA, lymphocytic choriomeningitis virus (LCMV) GPC and N proteins, Neurospora crassa activator protein, polyomavirus T antigen, simian virus 40 (SV40) small t antigen, SV40 large T antigen, Punta Toro phlebovirus N and Ns proteins, simian rotavirus VP6, CD4 (T4), human erythropoietin, Hantaan virus structural protein, human epidermal growth factor (EGF) receptor, human insulin receptor, human B lymphotrophic virus 130-kd protein, hepatitis A virus VP1, human tyrosine hydroxylase, human glucocerebrosidase, and mouse p53.

The term "promoter" means a DNA sequence which initiates and directs the transcription of a heterologous gene into an RNA transcript in cells.

The term "enhancer" means a cis-acting nucleic sequence which enhances the transcription of the structural gene and functions in an orientation and position-independent manner.

It is also contemplated that the expression of the heterologous gene may be enhanced by the expression of other factors, for example the IE-1 protein of nuclear polyhedrosis viruses.

It is further contemplated that the baculovirus artificial chromosome may include a DNA fragment encoding a secretion sequence functionally linked to the heterologous gene for the purposes of directing secretion of the heterologous protein out of the insect cell. In this case, the secretion sequence must be linked in frame with the open reading frame of the heterologous gene. Suitable secretion sequences include signal peptides such as the chorion signal peptide, the bombyxin signal peptide, the honey bee pre-promelittin signal peptide. Secretion sequences may also include the juvenile hormone esterase gene as set forth in U.S. patent application Ser. No. 09/136,421, entitled INSECT SEQUENCES FOR IMPROVING THE EFFICIENCY OF SECRETION OF NON-SECRETED PROTEINS IN EUKARYOTIC CELLS, Attorney Docket Number 028722–169, filed concurrently herewith, which claims priority to U.S. Provisional Patent Application Ser. No. 60/056,871, filed Aug. 21, 1997, both of which are incorporated by reference herein in their entirety.

The term "functionally linked" or "functionally attached" when describing the relationship between two DNA regions simply means that they are functionally related to each other and they are located on the same nucleic acid fragment. A promoter is functionally attached to a structural gene if it controls the transcription of the gene and it is located on the same nucleic acid fragment as the gene. An enhancer is functionally linked to a structural gene if it enhances the transcription of that gene and it is functionally located on the same nucleic acid fragment as the gene.

The term "introduction" refers to either infection or transfection of insect cells.

The term "infection" refers to the invasion by pathogenic viral agents of cells where conditions are favorable for their replication. Such invasion can occur by placing the viral particles directly on the insect cell culture or by injection of the insect larvae with the recombinant virus or by oral ingestion of the viral particles by the insect. The amount of recombinant virus injected into the larvae will be from $10^2$ to $10^5$ pfu of non-occluded virus/larvae. Alternatively, larvae can be infected by the oral route using occlusion bodies carrying recombinant viruses. In general, the amount of occlusion bodies fed to the larvae is that amount which for wild-type viruses corresponds to the $LD_{50}$ for that species of baculovirus and insect host. The $LD_{50}$ varies with each species of baculovirus and the age of the larvae. One skilled in the art can readily determine the amount of occlusion bodies to be administered. Typically, the amount will vary from $10-10^6$ occlusion bodies/insect.

The term "transfection" refers to a technique for introducing purified nucleic acid into cells by any number of methods known to those skilled in the art. These include but are not limited to, electroporation, calcium phosphate precipitation, lipofection, DEAE dextran, liposomes, receptor-mediated endocytosis, and particle delivery. The chromosomes or DNA can also be used to microinject eggs, embryos or ex vivo or in vitro cells. Cells can be transfected with the chromosomes or with the DNA described herein using an appropriate introduction technique known to those in the art, for example, liposomes. In a preferred embodiment, the DNA is introduced into the insect cells by mixing the DNA solution with "LIPOFECTIN" (GIBCO BRL Canada, Burlington, Ontario) and adding the mixture to the cells.

Methodology

The invention is directed towards a baculovirus artificial chromosome, which chromosome is useful in the expression of heterologous protein.

It has been found that the inactivation of the lef-8 gene in the baculovirus chromosome results in a baculovirus which is able to replicate its genome, but which is unable to kill the host cell. Accordingly, the baculovirus artificial chromosome is maintained in the host cell and is distributed into daughter cells.

Inactivation of the lef-8 gene can proceed by a variety of methods. It is contemplated that the gene can be deleted either partially or in total or altered by mutations, insertions or translocations. In particular, a transplacement vector is generated containing the wild-type lef-8 gene and possibly also containing a portion of the baculovirus genome 5' and 3' to the lef-8 gene. The transplacement vector preferably also contains sequences which allow replication of the vector in bacteria, such as E. coli and a selectable marker gene for selection in the bacterial cell.

The wild-type lef-8 gene is then inactivated by deletion, mutation, insertion or translocation. All or part of the gene may be deleted by digesting the gene at suitable restriction sites, removing a portion of the gene and relegating the transplacement vector. Sufficient baculovirus DNA on either side of the lef-8 gene must remain in the transplacement vector to allow cross-over recombination of the transplacement vector with the wild-type baculovirus genome such that the wild-type lef-8 gene is replaced with the modified gene. Preferred restriction enzymes for deletion are unique restriction sites within the open reading frame.

Alternatively, the lef-8 gene may be modified by insertion or translocation. Insertional mutations are those in which one or more nucleic acid residues extraneous to the native lef-8 gene are introduced into a predetermined site in the target DNA. Commonly, insertional mutations are fusions of a heterologous gene to the lef-8 gene. For example, a heterologous gene may be inserted into a restriction site within the lef-8 gene, thereby disrupting production of the lef-8 gene. In a preferred embodiment, the inserted gene is the desired heterologous gene functionally linked to a promoter. It is contemplated that the insertion may include two or more genes under the control of the same or separate promoters. It is further contemplated that the genes may be functionally linked to enhancers or other regulatory DNA sequences and/or secretion sequences.

The lef-8 gene may be modified by the introduction of mutations. Inactive genes ordinarily are prepared by site specific mutagenesis of nucleotides in the DNA encoding the lef-8 gene. The inactive genes can include substitutional variants of specific nucleic acids which result in the creation of internal stop codons resulting in the premature termination of translation of the mRNA transcribed from the gene. Alternatively, it is contemplated that the mutations may result in amino acid substitutions in the protein which inactivate the protein.

It is further contemplated that the lef-8 gene may be inactivated by the methods set forth above, prior to insertion into the transplacement vector.

An appropriate transplacement fragment or transplacement vector containing the inactivated lef-8 gene is constructed. Host insect cells, previously transformed with a lef-8 gene and capable of expressing the LEF-8 protein, are transfected simultaneously with wild-type viral DNA and the transplacement fragment or vector DNA containing baculovirus DNA sequences having the inactivated lef-8 gene and portions of the baculovirus homologous to the wild-type viral lef-8 gene. The genetic recombination system of the host insect cell recombines the plasmid and viral DNAs. Double crossover recombination events at homologous DNA sites results in the replacement of sequences of the viral genome with a portion of the transplacement fragment DNA, thereby inserting the recombinant expression cassette DNA containing the heterologous gene into the preferred site of the viral genome. Where the transplacement fragment or vector contains DNA sequences from the lef-8 gene or its flanking regions, a double recombination/crossover event between the homologous viral sequences in the transplacement fragment and the wild-type baculovirus genome will result in the inactivated or deleted lef-8 gene replacing the lef-8 gene of the wild-type genome. Following amplification of serially diluted progeny viruses, recombinant viruses are selected by hybridization to heterologous gene probes and confirmed by restriction endonuclease and DNA sequence analysis identification techniques. In the case of lef-8 gene substitution, cells containing recombinant viruses with double crossovers can be also identified visually because they do not kill the insect cells. If the cells express a detectable marker, they may also be detected on the basis that they fluoresce (green fluorescent protein gene) or stain blue on the appropriate medium (β-galactosidase gene).

It is further contemplated that the desired heterologous gene may not be inserted into the lef-8 gene but instead inserted into the baculovirus genome at a different location which allows such insertions. Suitable genes for the insertion of a heterologous gene would include, for example, the polyhedrin protein gene region, the p10 protein gene or any other neutral location which does not disrupt a crucial baculovirus function other than the lef-8 gene. The DNA sequence of the desired baculovirus insertion site would be obtained and introduced into a new transplacement vector. The heterologous gene under the control of a promoter would be inserted into the recombinant baculoviral insertion site present in the transplacement vector by methods known in the art, for example by insertion into an appropriate restriction enzyme site. The transplacement vector would then be transfected into the appropriate host cell with the baculovirus artificial chromosome and cross-over recombination would occur resulting in replacement of the baculovirus insertion site on the baculovirus artificial chromosome (having the lef-8 gene deleted) with the heterologous gene, thereby generating a baculovirus artificial chromosome containing a heterologous gene. It is contemplated that the heterologous gene may be inserted into a wild-type baculovirus chromosome first and then the inactivated lef-8 gene inserted into the recombinant chromosome. In either case, the resulting recombinant artificial chromosome will have the lef-8 gene inactivated and contain a heterologous gene.

The baculovirus artificial chromosome containing the heterologous gene would be propagated under suitable conditions to allow expression of the heterologous gene and production of the heterologous protein. Such conditions include a temperature range from 20° C. to about 40° C., and a pH of from 5 to about 8.

It is further contemplated that the baculovirus artificial chromosome having the heterologous gene could be propagated in an insect cell line in which the lef-8 gene is expressed. Such a cell line would allow the baculovirus artificial chromosome to complete the entire baculovirus cycle, producing infectious viruses and cell death. It is further contemplated that such infectious viruses could be used to infect insects (thus resulting in infection of germ cells and generation of transgenic insects by mating), insect or mammalian tissue culture.

A cell line in which the lef-8 gene is expressed may be generated by introduction of the lef-8 gene under the control of an appropriate promoter into the insect cell chromosome. Methods for the introduction of the lef-8 gene are disclosed in U.S. patent application Ser. No. 08/608,617, now U.S. Pat. No. 5,759,809, which is incorporated herein in its entirety. It is contemplated that the expression of the lef-8 gene may be induced. The expression may be functionally linked to another control element. For example, the lef-8 gene may be linked to a heat shock promoter or another inducible promoter.

Utility

This technology has several broad applications. For the generation of transgenic lepidopteran insects, baculovirus artificial chromosomes carrying useful genes can be used to transduce insect embryos by mating (sexual reproduction) for scientific study and applications in the biopesticide industry. For recombinant protein production in whole insects or in in vitro cell cultures, baculovirus artificial chromosomes could be used to efficiently deliver and express useful gene products for medical, research, and veterinary applications.

It has been found that the artificial baculoviral chromosome DNA can be used to transfect mammalian cells by methods known in the art. Furthermore, baculoviruses have been shown to infect non-productively mammalian cells. Therefore, it is contemplated that infectious baculoviruses, containing the baculovirus artificial chromosome could be used to transduce human tissue with therapeutic genes. Thus it is contemplated that baculovirus artificial chromosomes could be used for human gene therapy and DNA vaccination.

As can be appreciated from the disclosure above, the present invention has a wide variety of applications. Accordingly, the following examples are offered by way of illustration and not by way of limitation.

EXAMPLES

In the examples below, the following abbreviations have the following meanings. If not defined below, then the abbreviations have their art recognized meanings.

ORF—open reading frame
kb—kilobase
mg—milligram
ML—milliliter

Chemicals used in the following examples were obtained from the following companies:

Amersham Canada Ltd., Oakville, Ontario, Canada
J.T. Baker, Phillipsburg, N.J.

BioRad Laboratories Ltd. Canada, Mississauga, Ontario, Canada Boehringer Mannheim, Laval, Quebec, Canada Eli Lilly & Company, Indianapolis, Ind.

GIBCO BRL Canada, Burlington, Ontario, Canada

Hyclone Laboratories, Inc., Logan, Utah

JRH Biosciences, Inc., Lenexa, Kans.

Life Technologies, Burlington, Ontario, Canada

New England Biolabs, Inc., Mississauga, Ontario, Canada

Pharmacia LKB, Baie d'Urfe', Quebec, Canada

Promega Corporation, Madison, Wis.

Sigma, St. Louis, Miss.

Stratagene, La Jolla, Calif.

United States Biochemicals, Cleveland, Ohio

All enzymes used for the construction and characterization of the recombinant plasmids and baculoviruses were obtained from Pharmacia, LKB; New England Biolabs, Inc.; GIBCO BRL Canada; Boehringer Mannheim; and used according to those suppliers recommendations.

The cloning procedures set forth in the examples are standard methods described in Sambrook et al., *Molecular Cloning: A Laboratory Manual*, Cold Spring Harbor Laboratory (1982) which is incorporated herein by reference. This reference includes procedures for the following standard methods: cloning procedures with *E. coli* plasmids, transformation of *E. coli* cells; plasmid DNA purification, agarose gel electrophoresis, restriction endonuclease digestion, ligation of DNA fragments and other DNA-modifying enzyme reactions.

The procedures used to manipulate the baculoviruses are standard methods described in D. R. O'Reilly, L. K. Miller and V. A. Luckow, *Baculovirus Expression Vectors: A Laboratory Manual*, New York W.H. Freeman and Co., (1992) 347pp, which is incorporated herein by reference in its entirety. This reference includes procedures for the following standard methods: growth of baculovirus on tissue culture, transfection of insect cells with baculovirus DNA, titration and purification of recombinant baculoviruses by serial dilution and plaque assays, infection of insect cells and insect with infectious baculovirus.

Example 1

Analysis of a Temperature Sensitive Mutant of the Baculovirus BmNPV

Experiments in *Bombyx mori* Bm5 cell cultures have confirmed that a temperature sensitive mutation in the lef-8 gene of BmNPV prevents BmNPV from progressing into its virulent phase while allowing its genome to replicate at the non-permissive temperature.

*Bombyx mori* Bm5 silkworm tissue culture cells (Grace, 1967) were maintained in IPL41 medium (JRH Biosciences, Inc.) containing 10% fetal calf serum (Hyclone Laboratories, Inc.), as previously described (Iatrou et al., 1985).

The temperature sensitive mutation in the lef-8 gene of BmNPV baculovirus was obtained by chemical mutagenesis.

The temperature sensitive baculovirus was used to infect *Bombyx mori* Bm5 cells. Bm5 cells to be infected with virus were seeded into 6-well culture dishes at a density of $10^6$ cells (in 1 ml medium) per well. After overnight incubation the medium was removed and 1 ml of viral inoculum at a multiplicity of 10 was added to each well. The virus was left for 1 hour at room temperature, the cells were washed and 2 ml of fresh medium was placed on the cells. The cells were placed at the non-permissive temperature of 33° C. for up to 10 days with samples being taken at the times indicated in FIGS. 2A and 2B.

Figure 2A:
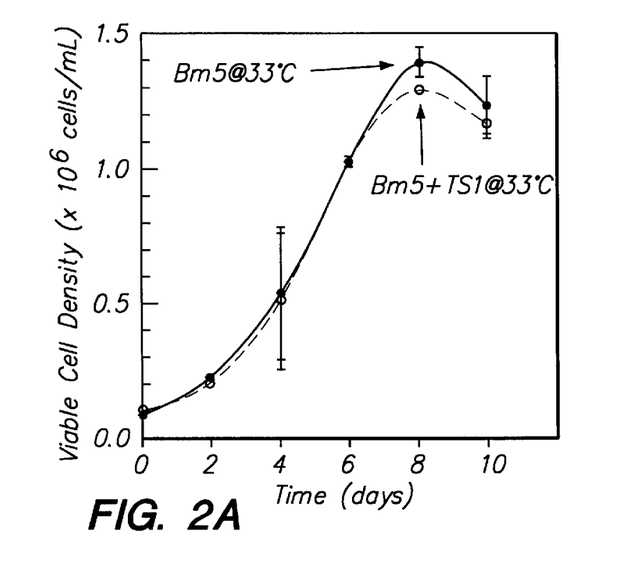
FIG. 2A compares the cell viability of normal uninfected Bombyx mori Bm5 cell cultures with Bm5 cells infected with a BmNPV temperature sensitive baculovirus (TS1) which has a mutation in the lef-8 gene when the cell cultures are maintained at non-permissive temperatures of 33° C.

The growth of the cells infected with either the wild-type virus or the temperature sensitive virus was measured by suspending the cells and counting the cells using the trypan blue exclusion method. FIG. 2A shows that, when maintained at the non-permissive temperature of 33° C., Bm5 cells infected with the temperature sensitive lef-8 mutant BmNPV (BM5 +TS1 in FIG. 2A) appear physiologically normal, as evidenced by the lack of significant differences in their growth compared to uninfected cells.

Viral DNA was obtained from the infected insect cells at various times after infection by lysing the cells. Cells were pelleted from the medium at 3000×g for 5 minutes, suspended in 1 ml PBS (10 mM $KH_2PO_4$, 2 mM $NaH_2PO_4$, 140 mM NaCl, 40 mM KCl) and repelleted. The cells were then suspended in 1 ml of PBS and an aliquot was dot-blotted onto Hybond N+ nylon membrane. The cells were lysed on the membrane and their RNA content hydrolyzed in 0.2 M NaOH for 3 cycles of 15 minutes. The membrane containing the lysed cells was washed in 0.25 M Tris-HCl (pH 7.8) for 2 cycles of 5 minutes and baked for 1 hour at 80° C.

Figure 2B:
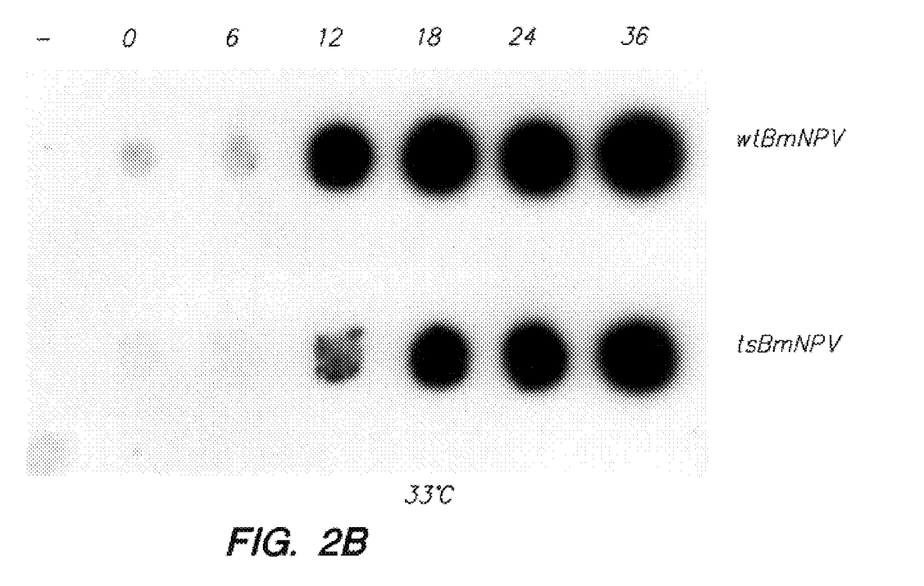
FIG. 2B illustrates a dot blot hybridization of BmNPV genomic DNA, taken at various times after infection from insect cells held at 33° C. infected with either a BmNPV temperature sensitive baculovirus which has a mutation in the lef-8 gene (tsBmNPV) or wild-type BmNPV (wtBmNPV) baculovirus.

The membrane was probed with $^{32}p$ radioactively labelled wild-type viral BmNPV DNA. FIG. 2B shows that the temperature sensitive lef-8 mutant BmNPV (tsBmNPV) can replicate its genome in the host cells at 33° C. in a manner that is very similar, if not identical, to the replication of a wild type BmNPV (wtBmNPV) containing a normal lef-8 gene.

Figure 2C:
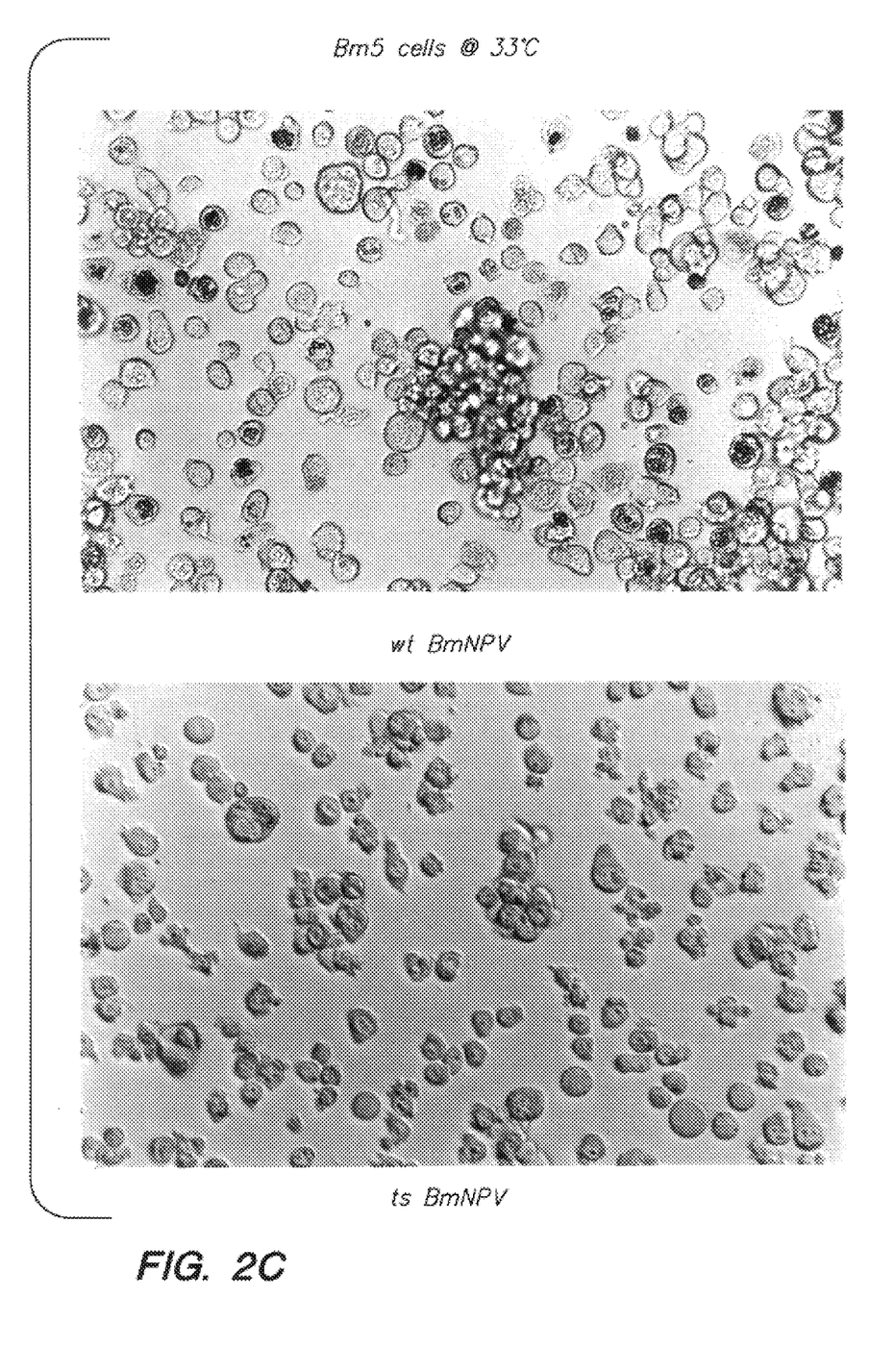
FIG. 2C is a photograph of Bm5 insect cells maintained at 33° C. three days after infection with wild-type BmNPV (wtBmNPV) or with the temperature-sensitive mutant of BmNPV (tsBmNPV). This figure illustrates that the mutant BmNPV is unable to progress into the virulent phase of infection, as evidenced by the lack of inclusion bodies 3 days after infection.

The *Bombyx mori* Bm5 insect cells BmNPV were observed in the microscope three (3) days after infection with either the temperature-sensitive BmNPV or with the wild-type BmNPV. FIG. 2C shows that the temperature sensitive lef-8 mutant BmNPV maintained at the non-permissive temperature of 33° C. is unable to progress into the virulent phase of infection, as evidenced by the absence of occlusion bodies 3 days after infection. In contrast, cells infected with wild type BmNPV contain occlusion bodies 3 days after infection at 33° C.

Example 2

Plasmid Constructions

The vector, pBmA is a pBluescript (Stratagene) derivative of clone pA3–5500 which contains the A3 cytoplasmic actin gene of *Bombyx mori* (Mounier and Prudhomme, 1986). Plasmid pBmA was constructed to contain 1.5 kb of the A3 gene 5' flanking sequences and part of its first exon to position +67 (relative to transcription initiation), a polylinker region derived from plasmid pBluescript (Stratagene) for insertion of foreign gene sequences, and an additional 1.05 kb of the A3 gene sequences encompassing part of the third exon of the gene from position +836 and adjacent 3' flanking sequences which contain signals required for RNA transcript polyadenylation. See U.S. patent application Ser. No. 08/608,617, now U.S. Pat. No. 5,759,809, which is incorporated by reference herein in its entirety.

This expression vector was constructed by (1) subcloning into plasmid Bluescript SK+ (Stratagene) a 1.5 kb KpnI/AccI fragment of clone pA3-5500 containing the 5' flanking, 5' untranslated and coding sequences of the A3 gene up to position +67 to generate plasmid pBmAp; (2) mutagenizing the ATG translation initiation codon present at position +36 to +38 of the actin coding sequence in plasmid pBmAp into AGG, AAG or ACG by the method of Kunkel (1985) to generate plasmids pBmAp.AGG, pBmAp.AAG and pBmAp.ACG; (3) subcloning into plasmid pSP72 (Promega Corporation) a 1.05 kb XhoI/SalI fragment of clone pA3-5500, containing part of the third exon of the actin gene from position +836 and adjacent 3' flanking sequences which include signals required for RNA transcript polyadenylation, to generate plasmid pBmAt; (4) converting the unique XhoI site of plasmid pBmAt into a NotI site by digestion of this plasmid with XhoI (GIBCO BRL), and end-filling with Klenow DNA polymerase (Boehringer Mannheim), ligation of NotI linkers (DNA Synthesis Laboratory.

The expression plasmid pIE1/153A contains the *Bombyx mori* cytoplasmic actin cassette (Johnson et al., 1992; U.S. patent application Ser. No. 08/608,617, now U.S. Pat. No. 5,759,809), *Bombyx mori* Nuclear Polyhedrosis Virus (BmNPV) HR3 enhancer element and the BmNPV ie1 gene and was constructed as follows. A 1.2 kb SspI fragment corresponding to the BmNPV genomic region from 51.8 to 52.7 map units containing the BmNPV HR3 element was cloned into the SmaI site of pBluescript-SK+ (Strategene) to yield plasmid p153. The plasmid pIE1/153 was made by inserting a 3.8 kb ClaI fragment containing the ie1 gene into the ClaI site of plasmid p153 removing unwanted restriction sites in the polylinker of this plasmid by double digestion with SacII and BamHI, blunt ending with T4 DNA polymerase and self-ligating the resultant plasmid. A 2.2 kb SacI fragment containing the actin cassette from the plasmid pBmA (Johnson et al., 1992) was ligated into the unique SacI site of plasmid pIE1/153 to yield the expression plasmid pIE1/153A.

Example 3

Generation of a Packaging Cell Line which Constitutively Expresses the Baculovirus lef-8 gene The wild-type BmNPV lef-8 open reading frame (BmNPV ORF #39) was obtained by PCR amplification using Pfu polymerase, wild-type BmNPV DNA as a template, and the following mutagenic PCR primers (SEQ ID NOS: 1 and 2):

I. 5' CAAAGGATCCGATGACGGACGTAG 3'

II. 5' CTTTTCTAGAGTTATCAATTTTTCATTATCG 3'

The 2.6 kbp PCR product was digested with BamHI/XbaI, and cloned into the unique BamHI/XbaI cloning sites of the expression plasmid pIE1/153 to yield the plasmid pIE1/153A.Lef8.

To generate the Bm5.LEF-8 cell line an antibiotic resistance plasmid was also constructed. A 1.4 kbp fragment containing the hygromycin B resistance gene was isolated from the plasmid pT676 (McAllister et al., (1990) *Gene*, 80:285; obtained from Eli-Lilly) and inserted into the BamHI site of pBmA, yielding the vector pBmA.HmB.

One million Bm5 cells were co-transfected in 6-well plates with a 100:1 molar ratio of the plasmids pIE1/153A.Lef8 to pBmAHmB using lipofection reagent (Life Technologies) according to the manufacturer's instructions. After 48 hours recovery following transfection, cells were subcultured weekly in the presence of 0.25 mg/mL hygromycin B (Boehringer-Mannheim) to eventually obtain a population of transformed cells. The Bm5.LEF-8 clone was isolated from the population by limiting dilution, and identified by its ability to rescue the temperature sensitive mutant virus at the non-permissive temperature of 33° C., as evidenced by the presence of occlusion bodies.

The resulting cells (Bm5.LEF-8 cells), produce the lef-8 protein constitutively.

Example 4

Generation of lef-8 Deficient Baculoviruses

In order to obtain mutant BmNPV containing an inactivated version of the lef-8 gene or lacking this gene completely, three transfer vectors, TV#1.LacZ; TV#2.LacZ, and TV#3.LacZ were generated. The DNA of the transfer vectors TV#1.LacZ and TV#2.LacZ was used in conjunction with DNA from wild type BmNPV, to generate the two respective recombinant baculoviruses BVAC#1.LacZ and BVAC#2.LacZ, described below) by co-transection of a Bm5 cell line stably transformed and constitutively expressing the polypeptide encoded by the lef-8 gene of BmNPV.

Figure 3:
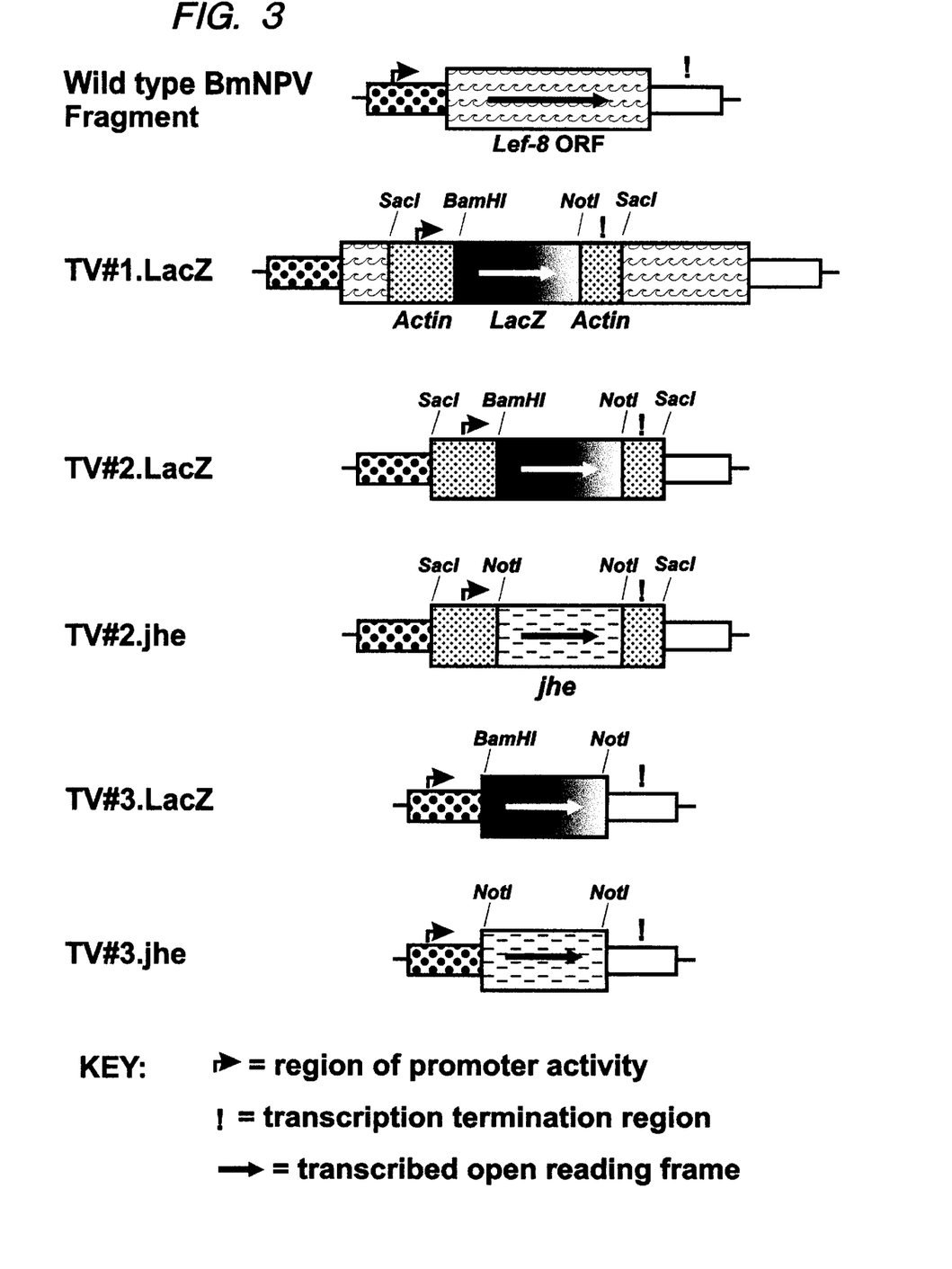

The two transfer vectors that were generated contain experimentally manipulated versions of the lef-8 gene. A schematic of the portions of the genome of BmNPV that these two transfer vectors contain is shown in FIG. 3. While the relevant portion of the genome of wild type BmNPV has a normal lef-8 gene, transfer vector TV#1.LacZ (FIG. 3) contains a construct expressing the reporter protein β-galactosidase under the control of the cytoplasmic actin gene promoter of the silkmoth *Bombyx mori* inserted at a point located 1,008 bp downstream from the ATG initiation codon of the lef-8 open reading frame. The second transfer vector, TV#2.LacZ, contains a construct expressing the reporter protein β-galactosidase under control of the *Bombyx mori* actin gene promoter, substituting for the complete lef-8 open reading frame (ORF).

The transfer vector TV#1A was generated as follows. First the 0 fragment from the HindIII digested wild-type BmNPV (Maeda and Majima (1990), *J. of Virology*, 71:1851–1855), containing some of the lef-8 open reading frame, was cloned into pBluescript(KS+). This plasmid was digested with SphI restriction enzyme, cutting at a site approximately 1009 bp from the start of the lef-8 open reading frame, blunt ended with T4 DNA polymerase, and ligated with a SacI linker. Next, some unwanted restriction sites remaining in the Bluescript polylinker region of the resulting plasmid (such as SacI) were removed by SacI partial digestion, EcoRV partial digestion, blunt ending and self ligation. Next, the Sacd fragment containing the actin cassette from pBmA was cloned into this plasmid to yield the plasmid TV#1A.

The transfer vector TV#2A was generated in three steps as follows:

a) PCR amplification using Pfu polymerase, wild-type BmNPV as a template and the mutagenic primers (SEQ ID NOs: 3 and 4),

I. 5'-GAAGGCAGCTGCGGCCCTCACGCGT-3'

II. 5'-GGAGGAGCTCTTGCACGATTGCAAACA TGATAAAACCG-3' yielded a 2.1 kb fragment flanking the 3' end of the lef-8 open reading frame. This was digested with SacI and PvuII and cloned into pBluescript SK+ that had been partially digested with PvuII and SacI.

b) PCR amplification using Pfu polymerase, wild-type BmNPV as a template and the following mutagenic primers (SEQ ID NOs: 5 and 6)

I. 5'-GGGGGGAGCTCGTAAAGCGATTATTGC ACACTAATTATGTC-3'

II. 5'-GAAAGGGTACCGTCGCGGACCATACGT TC-3' yielded a 2.0 kb fragment flanking the 5' end of the lef-8 open reading frame. This was digested with KpnI and SacI and cloned into the plasmid generated into (a).

c) The SacI fragment containing the actin cassette from pBmA was cloned into the plasmid resulting in b) to yield the plasmid TV#2A.

A 3.2 kb SpeI/BamHI fragment containing the lacZ open reading frame from pD16.43 (Fire et al., (1990), Gene, 93:189–198) was first cloned into the pBmA to yield pBmA-LacZ. From a BamHI/NotI digestion of pBmALacZ, a 3.2 kb fragment was ligated into the actin cassette of TV#1A and TV#2A to yield transfer vectors TV#1.LacZ and TV#2.LacZ, respectively, expressing LacZ for the generation of recombinant baculoviruses.

The third transfer vector, TV#3.LacZ, contains a construct capable of expressing foreign genes under the control of the native lef-8 promoter substituting for the complete lef-8 open reading frame in BmNPV.

The transfer vector TV#3.LacZ was generated as follows.

a) TV#2A was digested with SacI to remove the actin insert.

b) PCR amplification using pfu polymerase, pBluescript-SK+ as a template and the mutagenic primers (SEQ ID NOS: 7 and 8)
  1. 5'-ACCCTCACTAAAGGGAACAAAAGC-3'
  2. 5'-CTTTGAGCTCGAGGTCGACGG-3' yielded a 130 bp product containing a multiple cloning site polylinker that was digested with SacI and cloned into the unique SacI site of the plasmid from step (a) to form the plasmid TV#3P. From a BamHI/NotI digestion of pBmALacZ, a 3.2 kb fragment containing the LacZ gene was ligated into TV#3P to form TV#3.LacZ. The multiple cloning site in TV#3.LacZ has the same orientation with respect to the BmNPV lef-8 gene promoter as the multiple cloning site in pBmA has with respect to the actin gene promoter.

Recombinant BVAC#1.LacZ and BVAC#2.LacZ were subsequently generated following co-transection of the Bm5.LEF-8 cells with DNA from the two transfer vectors, TV#1.LacZ and TV#2.LacZ, respectively, and wild type BMNPV, and purified by serial dilution on the basis of β-galactosidase staining assays using the same cells. Cotransfection was accomplished by the methods set forth in Example 2.

The purified virus was propagated by infecting Bm5.LEF-8 cells grown in 25 cm$^2$ flasks at a density of 1×10$^6$ cells/ml. The medium from the infected cells, containing recombinant virus, was collected 4 to 7 days post infection and used as inoculum for subsequent experiments.

When infected with BVACs, the expression of lef-8 protein by Bm5.LEF-8 cells allows the mutant viruses to complete their life cycle and generate viral progeny after incubation at 28° C.

Supernatants from BVAC-infected Bm5.LEF-8 cells contain amplified BVACs, that are incapacitated in their ability to express the lef-8 gene product but express β-galactosidase. Such BVACs can be used to infect normal cells or insects.

Example 5

Expression of Heterologous Genes in a lef-8 Deficient Baculovirus

Figure 4A:
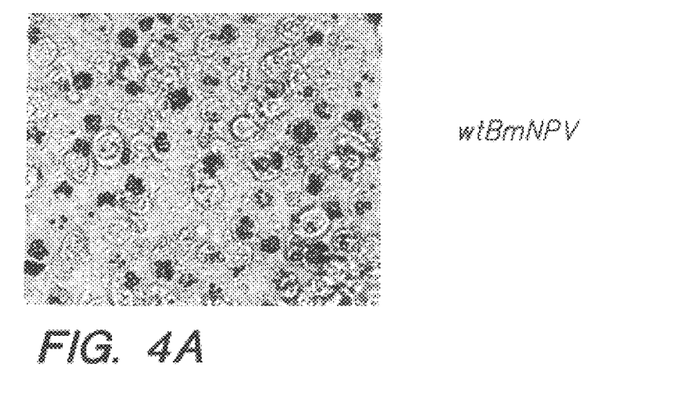
Figure 4B:
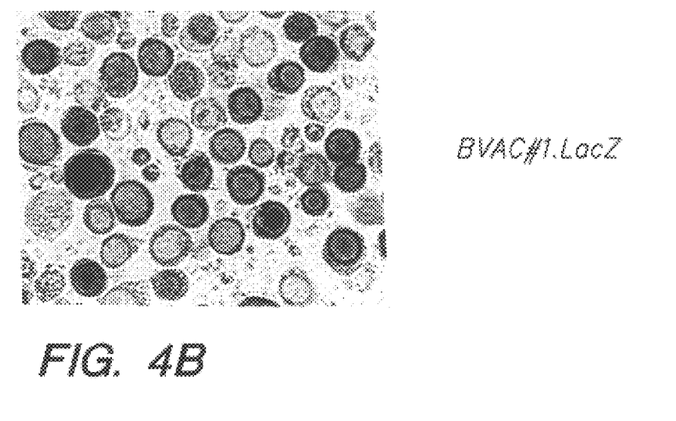
Figure 4C:
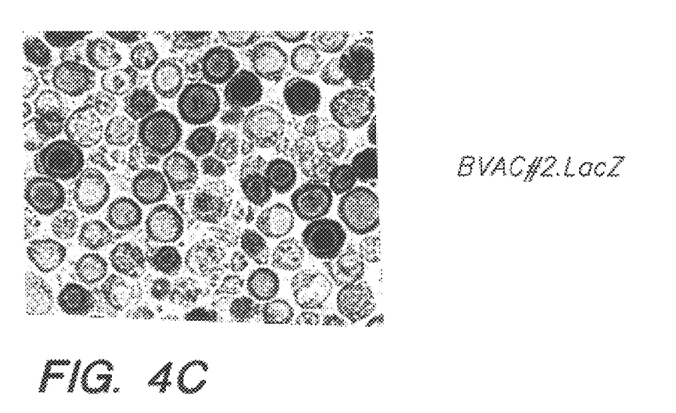

Normal Bm5 cells were infected with supernatant containing each of the three viruses: wild type, BVAC#1.LacZ and BVAC#2.LacZ, and incubated for 3 days at 28° C. The results are shown in FIG. 4, parts A to C. Bm5 cells infected with wild type BmNPV show occlusion bodies, indicating that wild type BmNPV could complete its infection cycle but do not produce β-galactosidase (FIG. 4A). Bm5 cells infected with BVAC#1.LacZ, do not show the presence of occlusion bodies, indicating that this virus is unable to complete its infection cycle, but stain for β-galactosidase (dark cells)(FIG. 4B), indicating that this virus is present in the cells and is able to express β-galactosidase. Similarly, Bm5 cells infected with BVAC#2.LacZ, do not contain occlusion bodies, indicating that this virus did not complete its infection cycle and also stain for β-galactosidase (dark cells)(FIG. 4C), indicating that this virus is present in the cells.

Example 6

Expression of Juvenile Hormone Esterase in Cells

To demonstrate that the TV#3 construct is capable of expressing a foreign gene in the presence of baculovirus infection, the reporter gene juvenile hormone esterase (JHE, Bonning and Hammock, (1995) *J. Vir. Meth*. 51:103–114) was used. A 1.8 kbp NotI fragment from pIE1/153A.jhe(kk) (Lu et al., (1997) *J. Biol. Chem*. 272:30724–30728) containing the JHE open reading frame was ligated into the unique NotI sites of both TV#2A and TV#3P to yield the plasmids TV#2.jhe and TV#3.jhe; respectively.

Figure 5:
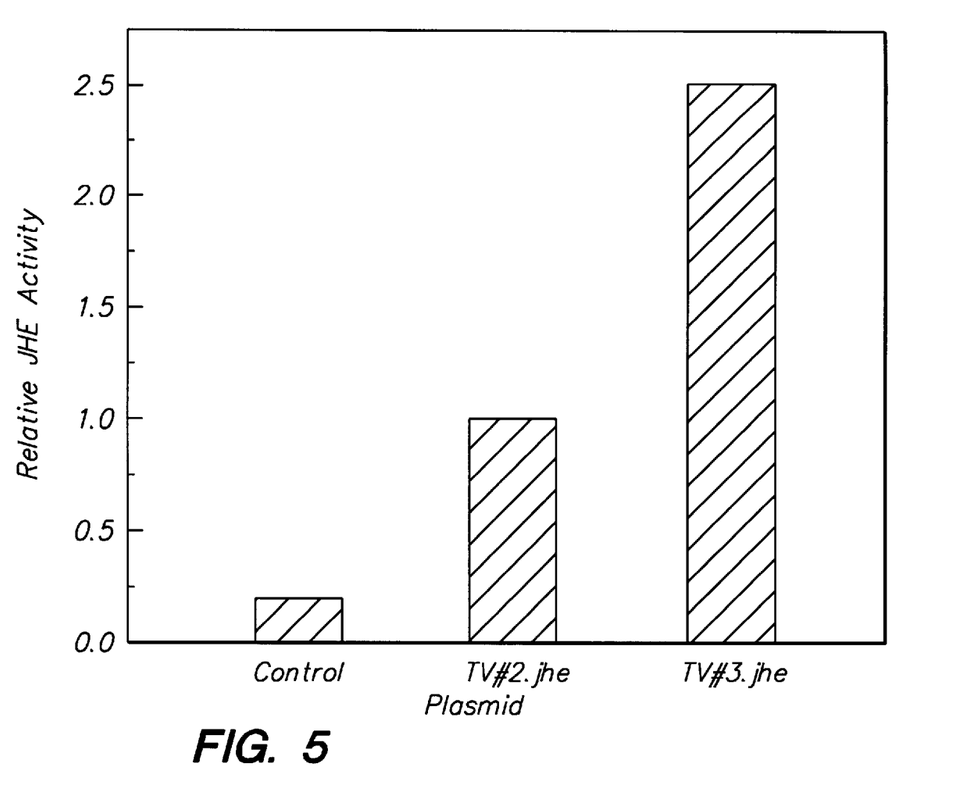
FIG. 5 is a graph showing the relative juvenile hormone esterase activity of cells infected with wild-type BmNPV immediately followed by transfection with TV#2.jhe and TV#3.jhe.

One million Bm5 cells in 6-well plates were infected with BmNPV at a multiplicity of infection of 5 viruses per cell for 1 hour. Cells were then transfected with the plasmids TV#2.jhe or TV#3.jhe using lipofectin reagent (Life Technologies) according to the manufacturer's instructions. Sixty hours following transfection, the supernatant was tested for JHE activity using JHE activity assays (Philpott and Hammock, (1990) *Insect Biochem*. 20:451–459). FIG. 5 reveals that supernatant from TV#3.jhe transfected cells contains approximately 2.5 fold more jhe activity than from TV#2.jhe transfected cells. The supernatant from mock-transfected cells (control) contained background juvenile hormone esterase activity.

This indicates that the TV#3P contains DNA elements capable of expressing a foreign gene in the presence of baculovirus infection and would be useful for generating a baculovirus artificial chromosome.

From these experiments, a baculovirus artificial chromosome has been created which is an infectious, yet harmless, self-replicating extra-chromosomal entity, capable of carrying useful genes of scientific or commercial value into lepidopteran insect cells.

While the present invention has been described with reference to what are considered to be the preferred examples, it is to be understood that the invention is not limited to the disclosed examples. To the contrary, the invention is intended to cover various modifications and equivalent arrangements included within the spirit and scope of the appended claims.

REFERENCES

All publications, patents and patent applications are herein incorporated by reference in their entirety to the same extent as if each individual publication, patent or patent application was specifically and individually indicated to be incorporated by reference in its entirety.

Sambrook et al., *Molecular Cloning: A Laboratory Manual*, Cold Spring Harbor Laboratory (1982)

Bonning and Hammock (1995). *J. Vir. Method*. 51:103–114

Fire et al., (1990) *Gene*, 93:189–198

Grace (1967) "Establishment of a line of cells from the silkworm *Bombyx mori*" *Nature* 216:613

Hashimoto et al., (1996), "Attenuation of *Bombyx mori* nuclear polyhedrosis for a gene transfer vector", p70 in Japan-Canada Cooperative Workshop Iatrou et al. (1985) "Polyhedrin gene of *Bombyx mori* nuclear polyhedrosis virus", *J. Virol* 54:436445;

Johnson et al., (1992) *Virology* 190:815–823

Lu et al., (1997) *J. Biol. Chem.* 272:30724–30728

Maeda and Majima (1990) *J. of Virology*, 71:1851–1855

Mounier and Prudhomme, (1986) *Biochimie*, 68:1053–1061

Kunkel (1985) *P.N.A.S.*, 82:488–492

McAllister et al., (1990), *Gene*, 80:285

D. R. O'Reilly, L. K. Miller and V. A. Luckow, *Baculovirus Expression Vectors: A Laboratory Manual*, New York W.H. Freeman and Co., (1992) 347pp Philpott and Hammock (1990) *Insect Biochem* 20:451–459

---

What is claimed is:

1. An baculovirus artificial chromosome lacking a gene encoding an active LEF-8 protein.

2. The baculovirus artificial chromosome according to claim 1 wherein the lef-8 gene is deleted.

3. The baculovirus artificial chromosome according to claim 1 wherein the chromosome comprises an inactivated lef-8 gene.

4. The artificial chromosome according to claim 1 further comprising a heterologous gene.

5. The baculovirus artificial chromosome according to claim 1 wherein the chromosome is derived from the genome of BmNPV, AcNPV, OpNPV or any other baculovirus genome containing a lef-8 gene.

6. The baculovirus artificial chromosome according to claim 1 wherein the chromosome further comprises a detectable marker gene.

7. A baculovirus comprising the baculovirus artificial chromosome of claim 1.

8. A cell comprising the baculovirus artificial chromosome according to claim 1.

9. The baculovirus artificial chromosome according to claim 1 wherein the baculovirus chromosome is selected from the group consisting of the genomes of BmNPV, AcNPV and OpNPV.

10. A baculovirus comprising the baculovirus artificial chromosome of claim 4.

11. The cell according to claim 8 wherein the cell is a eukaryotic cell.

12. The cell according to claim 11 wherein the cell is an insect cell.

13. The cell according to claim 11 wherein the cell is an mammalian cell.

14. A method of making an baculovirus artificial chromosome, said method comprising inactivating the lef-8 gene of a baculovirus genome such that the baculovirus genome is unable to produce an active LEF-8 protein.

15. The method of claim 14 wherein the lef-8 gene is inactivated by deleting the gene from the baculovirus chromosome.

16. A method of expressing a heterologous gene in a eukaryotic cell, said method comprising propagating a eukaryotic cell comprising one or more baculovirus artificial chromosomes lacking a gene which encodes an active LEF-8 protein wherein said baculovirus artificial chromosome further comprises a DNA sequence encoding a heterologous gene, under conditions that allow expression of the heterologous gene.

17. The method according to claim 16 wherein the cell is an insect cell.

18. The method according to claim 16 wherein the cell is a mammalian cell.

19. The method according to claim 16 wherein the chromosome further comprises a detectable marker gene.

20. An insect cell comprising a lef-8 gene in the absence of a baculovirus chromosome and wherein the LEF-8 protein is produced.

21. The insect cell according to claim 20, wherein production of the LEF-8 protein is induced.

22. The insect cell according to claim 20 wherein the lef-8 gene is derived from the genome of BmNPV, AcNPV or OpNPV.

* * * * *